United States Patent [19]

Garnett et al.

[11] 4,172,838

[45] Oct. 30, 1979

[54] PREPARATION OF FURAN COMPOUNDS

[75] Inventors: Donald I. Garnett, Hockessin, Del.; Marvin L. Peterson, Woodstown, N.J.

[73] Assignee: E. I. Du Pont de Nemours and Company, Wilmington, Del.

[21] Appl. No.: 935,389

[22] Filed: Aug. 21, 1978

[51] Int. Cl.$^2$ ............................................ C07D 307/36
[52] U.S. Cl. ................................. 260/346.11; 252/441
[58] Field of Search .................................... 260/346.11

[56] References Cited

FOREIGN PATENT DOCUMENTS 52-152731  6/1977  Japan.
1263566    6/1970  U.S.S.R.

Primary Examiner—Richard Raymond

[57] ABSTRACT

A process for preparing a furan compound by the catalytic oxidation of a diolefin such as butadiene or a halo-substituted alkene is provided. In this process the starting material is contacted with an aqueous medium having a pH less than about 2 containing (1) iodide ion, (2) a mixture of cuprous and cupric ions, and (3) a solubilizing agent for cuprous ion such as an alkali metal halide. Optionally, an oxygen-containing gas such as air can also be contacted with the aqueous medium. In one embodiment, the starting material is contacted with an aqueous solution of the aforesaid ingredients in one reaction zone to prepare furan and a portion of the solution is passed to a second reaction zone where cuprous ion is oxidized to cupric ion with air and then the air-treated solution returned to the first reaction zone.

26 Claims, No Drawings

PREPARATION OF FURAN COMPOUNDS

DESCRIPTION

1. Technical Field

This invention relates to processes for the preparation of furan compounds, catalysts useful in the processes, and more particularly to processes for the preparation of furan compounds from diolefins and alkenes, particularly butadiene.

2. Background Art

Furan is a chemical useful in furan resins and, more importantly, as a raw material for the manufacture of tetrahydrofuran. However, furan today is prepared from natural pentose contained in corn or oat hulls through furfural as an intermediate. To reduce the cost of tetrahydrofuran, it is produced today from acetylene and formaldehyde through 1,4-butynediol and 1,4-butanediol as intermediates. While this is a satisfactory process, it is moderately complex in the number of steps required to reach tetrahydrofuran as the final product. More importantly, however, acetylene is becoming more expensive due to energy inefficiencies involved in its manufacture.

There have been attempts over the years to produce furan directly by the catalytic oxidation of butadiene. These attempts have generally been under harsh processing conditions, e.g., at temperatures higher than about 375° C., which result in overoxidation to carbon oxides and furan decomposition. Such high temperature, vapor phase processes are exemplified by U.S. Pat. Nos. 3,238,225; 3,716,545; 3,775,508; 3,864,279; 3,906,009; 3,912,763; 3,928,389 and 4,026,820.

A process for preparing furan by oxidation of butadiene with molecular oxygen at lower temperatures (40°–150° C.) either in a vapor phase reaction or a liquid phase reaction is described in Japanese patent application Publication No. 52-77049 dated June 29, 1977. In one aspect of the process described therein, a palladium salt and a thalium or indium salt are dissolved in acidified water and then butadiene and oxygen are passed through the solution. A similar process is described in Russian Pat. No. 265119 dated June 24, 1970. In this process, butadiene (or butadiene and air) is passed through an acidic, aqueous solution of cupric chloride and palladium chloride at a temperature of 60°–110° C. Cuprous chloride can be used in place of palladium chloride. Both of these processes suffer deficiencies of impractical rates of reaction and excessively low reaction life.

DETAILED DESCRIPTION

According to the present invention there is provided an improved process for preparing a furan compound by the oxidation of a diolefin or a mono- or dihalo-substituted alkene, wherein the improvement comprises contacting in a reaction zone (A) a diolefin of the formula:

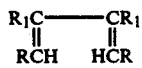

where
each R is H or an alkyl group of 1–4 carbon atoms, and
each $R_1$ is H, a halide or an alkyl group of 1–4 carbon atoms,
with the proviso that the total number of carbon atoms does not exceed 8,
or (B) a mono- or dihalo-substituted alkene of 4–8 carbon atoms, with an aqueous medium having a pH less than about 2 containing (1) iodine from elemental iodine or an iodine-containing compound, (2) copper having an average oxidation state between 1 and 2, and (3) a solubilizing agent for cuprous ion which is soluble in water and forms a water-soluble complex with cuprous ion.

In one embodiment of the present invention there is provided an improved process for preparing a furan compound by the catalytic oxidation of a diolefin, wherein the improvement comprises (1) continuously contacting in a first reaction zone a diolefin of the formula:

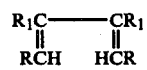

where
each R is H or an alkyl group of 1–4 carbon atoms, and
each $R_1$ is H, a halide or an alkyl group of 1–4 carbon atoms,
with the proviso that the total number of carbon atoms does not exceed 8,
with an aqueous medium having a pH less than about 2 containing (a) iodine from elemental iodine or an iodine-containing compound, (b) copper having an average oxidation state between 1 and 2 and (c) a solubilizing agent for cuprous ion selected from the group consisting of at least one of a metal halide, ammonium halide, halogen acid and organic solvent; (2) continuously removing reaction gases from the first reaction zone, removing furan compound product therefrom and returning unreacted diolefin to the first reaction zone; (3) continuously removing aqueous medium from the first reaction zone and passing it to a second reaction zone; (4) continuously contacting an oxygen-containing gas with the aqueous medium in the second reaction zone to oxidize cuprous ion in the aqueous medium to cupric ion; and (5) continuously returning oxygen-treated aqueous medium to the first reaction zone.

The present process for the preparation of a furan compound such as furan from a diolefin or a mono- or dihalo-substituted alkene uses a catalyst system comprising a mixture of cuprous and cupric ions, iodine and a solubilizing agent for cuprous ion contained in an aqueous medium. The system should contain at least 20 moles per liter of water. This process, which can be conducted at low temperatures and pressures, produces the furan compound at good conversions and yields and at practical rates of reaction.

A 1,3-diolefin or a mono- or dihalo-substituted alkene of 4–8 carbon atoms which forms the 1,3-diolefin in situ under the reaction conditions are used as the starting materials in the present process. In the following paragraphs these chemicals will be referred to as "starting materials."

The useful 1,3-diolefins have the formula:

where
each R is H or an alkyl group of 1–4 carbon atoms (preferably methyl), and
each $R_1$ is H, an alkyl group of 1–4 carbon atoms (preferably methyl) or a halide such as chloro or iodo (preferably chloro),
with the proviso that the total number of carbon atoms does not exceed 8, preferably does not exceed 5.

Illustrative diolefins are 1,3-butadiene; 1,3-pentadiene; chloroprene(2-chloro-1,3-butadiene); isoprene(2-methyl-1,3-butadiene); 2-iodo-1,3-butadiene; 1,3-hexadiene; 2,4-hexadiene; 2,3-dimethyl-1,3-butadiene; 3,4-dimethyl-2,4-hexadiene; 4,6-octadiene; and 1,3-octadiene. Of these diolefins, the first four listed are preferred due to commercial availability, with 1,3-butadiene being most preferred. Mixtures of diolefins can be used if desired.

Illustrative of the useful mono- or dihalo-substituted alkenes are: 1-chloro-2-butene; 3-chloro-1-butene; 1-iodo-2-butene; 1-chloro-2-pentene; 1-chloro-2-hexene; 3-chloro-1-pentene and 1-bromo-2-pentene. The preferred halo-substituted alkenes are the butenes with the most preferred being crotyl chloride; and if desired, mixtures can be used.

When used in the process of the invention, the starting material can be used undiluted, mixed with a gas inert to the reaction, such as nitrogen, carbon monoxide or carbon dioxide, or used with an oxygen-containing gas such as air. In a preferred embodiment of the invention, the starting material is mixed with the oxygen-containing gas, e.g., at about a 20–50 percent by volume starting material when the oxygen-containing gas is air. The starting material is then contacted with the above-mentioned aqueous medium in a reaction zone, under reaction conditions suitable for conversion to furan compounds, preferably with a molecular oxygen-containing gas.

The aqueous medium with which the starting material is contacted should have a pH less than about 2, as measured by any known type of pH measuring device. A pH meter with glass electrodes is typically used. Furan production is increased when the pH is less than about 0.5 and it is preferred that the pH be about 0.0 or less.

However, measurement of pH by glass electrodes in the aqueous solutions of copper salts which are used in the process of the invention does not accurately measure the molar concentrations of hydrogen ion. For example, the pH of a solution which is 0.1 Normal in hydrochloric acid and contains the concentrations of copper salts which are exemplified is below 0 when measured with a glass electrode. The molar concentrations of hydrogen ions in the mixes may be determined by titrations of aliquot samples dissolved in 10-fold quantities of water with standard base solutions. Standard techniques for determining the end-points of acid-base titrations may be used, i.e., by indicators, such as Congo red or methyl orange, or with a pH meter.

In the present process, the molarity of the hydrogen ion will preferably be greater than about 0.05, preferably in the range of about 0.1–1.0.

It is preferred that the aqueous medium be an aqueous solution with water being used as the only solvent; however, the term aqueous medium also means aqueous solutions in which the water is diluted with hydrophilic solvents such as acetic acid, sulfolane, acetonitrile, dioxane, and the like. Aqueous medium also includes those aqueous solutions in which an organic solvent is used as a cuprous ion solubilizing agent as discussed later.

The aqueous medium used in the present process contains (1) iodine, (2) a copper redox catalyst, i.e., a mixture of cuprous and cupric ions, and (3) a solubilizing agent to aid in keeping cuprous ion in solution.

Iodine is thought to be present in the aqueous medium as iodide ion which is typically added as elemental iodine or as an alkali metal iodide, preferably sodium iodide or potassium iodide. Since very little iodine is needed, any iodine-containing compound can be used which is at least partially soluble in the aqueous medium. Illustrative iodine-containing compounds are lithium iodide, calcium iodide, cuprous iodide, ferrous iodide, potassium iodate and hydiodic acid, and organic iodides such as methyl iodide and ethyl iodide. Of these, iodine from elemental iodine or alkali metal iodides are preferred. The concentration of iodine in the aqueous medium will normally be in the range of about $1 \times 10^{-12}$–0.5 gram mole per liter, preferably in the range of about 0.001–0.2 gram mole per liter.

The metallic component of the catalyst of the invention is copper. The copper in the aqueous medium has an average oxidation state between 1 and 2, i.e., the copper is a mixture of cuprous ion and cupric ion. Any copper compound soluble in the aqueous medium can be used, although copper halides such as the chlorides and bromides are preferred. Especially preferred is a mixture of cupric chloride and cuprous chloride even though either one alone can be added to the aqueous medium, in which event one can very quickly obtain a mixture of the two copper ions either through oxidation of cuprous to cupric or reduction of cupric to cuprous. The total copper concentration in the aqueous medium will usually be in the range of about 0.1–10 gram moles per liter, and normally about 0.5–3 gram moles per liter. Under preferred operating conditions, there will be a ratio of cupric ion to cuprous ion of 100:1 to 1:2, preferably 10:1 to 1:1. Illustrative copper compounds that can be used are halides of copper such as cupric chloride, cupric bromide, cuprous chloride, cuprous bromide and cuprous iodide; copper salts of organic acids, which may be carboxylic acids, such as acetic, propionic, pivalic, formic, succinic or adipic acids, fluorinated carboxylic acids, such as trifluoroacetic acid, sulfonic acids, such as methane sulfonic acid, benzenesulfonic acid and p-toluenesulfonic acid or fluorinated sulfonic acids, such as trifluoromethyl sulfonic acid; or salts of inorganic acids, such as cupric sulfate, cupric nitrate and cupric tetrafluoroborate.

In order to keep cuprous ion in solution, a solubilizing agent is used. A useful solubilizing agent is any inorganic or organic compound which is soluble in water and tends to form a water-soluble complex with cuprous ion. While alkali metal halides, alkaline earth metal halides, ammonium halides and halogen acids are preferred, other metal halides such as palladium halides and iron halides, and organic solvents can also be used. By halides it is meant the chlorides and bromides, and preferably the chlorides. Illustrative organic compounds are (1) organic nitriles including aliphatic nitriles such as acetonitrile, succinonitrile, and propionitrile and aromatic nitriles such as benzonitrile; (2) carboxylic acids such as acetic acid; (3) thiocyanates such as sodium thiocyanate; and (4) aromatic amines or their hydrochlorides such as tetramethylethylenediamine. It will be within the skill of the art to select a particular solubilizing agent and the appropriate amount to use. Especially preferred solubilizing agents are sodium chloride, calcium chloride and ammonium chloride.

The concentration of the solubilizing agent is typically in the range of about 0.01–5 gram moles per liter, preferably about 0.5–3 gram moles per liter.

The process of the invention can be carried out at a temperature in the range of about 50°–125° C., preferably 75°–105° C. and most preferably about 95°–103° C. As would be expected, rates of furan production are reduced at the lower temperatures. Reaction pressures are typically in the range of about 0.1–10 atmospheres, preferably about 1–3 atmospheres and most preferably at atmospheric pressure. It is the starting material's partial pressure in the gas stream contacted with the aqueous medium that can determine a particular pressure used.

The starting material flow rate through the aqueous medium does not appear to be critical. As will be apparent, the flow rate should not be so fast as to give inadequate contact time between the starting material and aqueous medium or so slow as to enable the resulting furan product time to decompose or polymerize. It is preferred that the aqueous medium be agitated either mechanically or by good gas dispersion in the aqueous medium, and the reaction off-gases containing furan product be removed from the reaction vessel promptly. The optimum contact time between the starting material and aqueous medium depends on many factors and is readily determined by one skilled in the art.

Since cupric chloride is very corrosive, the reactor for carrying out the process of the invention should be made of a material which is not corroded by the aqueous medium. Illustrative materials are glass or ceramic-lined metals, titanium, tantalum-clad metals, impregnated graphite tubes and the like.

In a preferred embodiment of the invention, an oxygen-containing gas is contacted with the aqueous solution, along with the starting material to oxidize cuprous ion formed to cupric ion. Typically, the starting material and oxygen-containing gas are mixed and then passed through the aqueous medium, although they can be fed as two separate gas streams. The oxygen-containing gas employed can be molecular oxygen as such, or molecular oxygen utilized with a diluent inert to the reaction such as nitrogen and the like. Typical molecular oxygen-containing gases are air, which is preferred, flue gases or synthesis gases which contain residual oxygen, and any source of molecular oxygen which is at least essentially free of contaminants which would be detrimental to the desired reaction. The amount of oxygen-containing gas used is sufficient to provide about 1–2 moles of molecular oxygen per mole of furan compound prepared.

Another preferred embodiment of the invention is a two-stage process wherein furan is produced in a first stage by contacting the starting material with the aqueous solution and cuprous ion is oxidized to cupric ion in a second stage by contacting the aqueous solution containing excess cuprous ion with the above-described oxygen-containing gas. This two-stage process can be conducted either intermittently in one reaction vessel or continuously in two reaction vessels.

In intermittent operation, the starting material is contacted with the aqueous medium until such time as furan production starts to decrease, the flow of starting material is stopped and then the oxygen-containing gas is contacted with the aqueous medium until essentially the original cupric ion concentration is reached. The course of the reaction can be monitored by following the acidity of the aqueous medium or by measuring the cuprous and cupric ion content.

In continuous operation, furan compound is produced in a first reaction vessel by continuously contacting starting material with the aqueous medium. The reaction gases, including unreacted starting material, inert gases and reaction products in addition to the desired furan compound are continuously removed from the reaction vessel, furan compound removed therefrom by conventional techniques and any unreacted starting material recovered and recycled to the first reaction vessel along with make-up starting material. The aqueous medium is continuously circulated as a working solution between the first reaction vessel, where the furan compound is produced, and a second reaction vessel, where an oxygen-containing gas (air) is contacted with the now cuprous ion-rich aqueous medium to oxidize cuprous ion therein to cupric ion. The oxygen-treated aqueous medium enriched with cupric ion is continuously returned to the first reaction vessel.

In the examples which follow, conversion of starting material, e.g., butadiene, is the mole percent of starting material fed which is converted to products. The furan yield is the mole percent of product which is furan. When operated under optimum conditions, the present process can achieve a conversion of starting material, e.g., butadiene, of about 10–90 percent and a furan yield of about 70–95 percent.

In the Examples samples for gas chromatographic analyses were collected in 1 ml Carle sampling loops from the product stream. The samples were injected by Carle sampling valves onto $10' \times \frac{1}{8}''$ columns of "Parapak N" for determination of their air, carbon dioxide, butadiene and furan contents. Analyses were carried out at 175° C. with helium carrier gas at 25 ml/min. The areas of the peaks in the chromatograph were converted to volume percents of components using factors determined by calibrations with known quantities of components.

EXAMPLE 1

A mixture of 50 percent by volume of butadiene and 50 percent by volume of nitrogen was fed at a rate of 80 ml/min through a fritted glass disc at the bottom of a glass reactor into 100 ml of an aqueous solution, having an initial pH of about 0.5, which was 2 molar in cupric chloride, 1 molar in cuprous chloride, 1.7 molar in sodium chloride, 0.24 molar in potassium iodide and 0.06 molar in hydrochloric acid. The solution was maintained at a temperature of 95° C. by an external heating jacket and was stirred with a vane disc stirrer. After 0.5 hour of operation, the gaseous product stream contained 10.9 percent by volume furan, as analyzed by gas chromatography (GC), produced at a rate of 8.7 ml/min. The conversion of butadiene to products was 20 percent and the yield of furan was 95 percent.

As a control without added iodine, butadiene was fed at a rate of 40 ml/min into the above stirred glass reactor which contained 100 ml of an aqueous solution having an initial pH at or below 0 which was 2 molar in cupric chloride, 2 molar in cuprous chloride and 4 molar in lithium chloride. The temperature was maintained at 95° C. After 1 hour of operation, the gaseous product stream contained 3 percent by volume furan analyzed by GC. Furan was produced at a rate of 1.2 ml/min.

EXAMPLE 2

Example 1 was repeated except the aqueous solution was 0.03 molar in potassium iodide. After 1 hour of operation, furan was being produced at a rate of 7 ml/min.

EXAMPLE 3

A mixture of 50 percent by volume of butadiene and 50 percent by volume of nitrogen was fed at a rate of 120 ml/min through a fritted glass cylinder located under a vaned disc stirrer in a 1 liter baffled flask reactor. The flask contained 400 ml of an aqueous solution at 95° C., having an initial pH of 2. The solution was 2.05 molar in cupric chloride, 0.5 molar in cuprous chloride, 0.86 molar in sodium chloride and 0.0075 in potassium iodide. Furan production in the gaseous product stream was followed by GC. The results are shown in Table I.

TABLE I

| Reaction Time Min | pH of Solution | Vol. % Furan in Exit Gases | Furan Prod. ml/min |
|---|---|---|---|
| 15 | 2.0 | 0.2 | 0.22 |
| 30 | 0.0 | 1.7 | 2.0 |
| 45 | −0.3 | 5.4 | 6.4 |
| 60 | <0.0 | 8.1 | 9.7 |
| 75 | <0.0 | 10.7 | 12.8 |
| 90 | <0.0 | 11.3 | 13.6 |

The conversion of butadiene was 22–30 percent and the yield of furan was 88 percent.

EXAMPLE 4

A gaseous stream of 50 percent by volume of butadiene in nitrogen was fed at a rate of 100 ml/min to the reactor of Example 1 containing 100 ml of an aqueous solution which was 2 molar in cupric chloride, 1 molar in cuprous chloride, 2 molar in calcium chloride and 0.04 molar in elemental iodine. The solution had an initial pH less than 2 and was maintained at a temperature of 95° C. The gaseous product stream contained 6.2 percent by volume of furan, as analyzed by GC, after 0.5 hour of operation. Furan production was at a rate of 6.2 ml/min.

EXAMPLE 5

Example 1 was repeated except the aqueous solution was 2 molar in cupric chloride, 1 molar in cuprous chloride, 2 molar in ammonium chloride and 0.12 molar in potassium iodide and had an initial pH of about 0.0. After about one hour of operation, furan was produced at a rate of 4.6 ml/min.

EXAMPLE 6

Example 1 was repeated except the aqueous solution was 2 molar in cupric chloride, 0.5 molar in cuprous chloride, 5.7 molar in lithium chloride and 0.12 molar in potassium iodide. Furan was produced at a rate of 1.7 ml/min after 0.5 hour of operation.

EXAMPLE 7

This example illustrates rates of furan production at increasing levels of cupric ion concentration in the aqueous solution.

A gaseous stream of 50 percent by volume butadiene in nitrogen was fed at a rate of 80 ml/min into reaction flask of Example 3 containing 400 ml of an aqueous solution, having initial pH less than 2, which was 0.5 molar in cupric chloride, 1.5 molar in cuprous chloride, 3 molar in sodium chloride and 0.3 molar in potassium iodide. At a reactor temperature of 100° C., the gaseous product stream contained 5 percent by volume of furan, as measured by GC, produced at a rate of 4 ml/min. The conversion of butadiene was 8 percent and the yield of furan was 85 percent.

The reaction was stopped, the cupric chloride concentration of the aqueous solution was increased to 1.2 molar, and then the flow of the butadiene-nitrogen gas stream resumed. The aqueous solution had a pH less than 0 and the reaction temperature was maintained at 103° C. After one hour of operation, the gaseous product stream was analyzed by GC at 15.1 percent by volume furan at a production rate of 12 ml/min. The conversion of butadiene to product was 32 percent and the yield of furan was 87 percent.

Again the reaction was stopped and the cupric chloride concentration of the aqueous solution increased, this time to 1.53 molar. The flow of the butadiene-nitrogen gaseous stream was resumed. At a reactor temperature of 104° C. and a solution pH less than 0, the gaseous product stream contained 22 percent by volume furan produced at a rate of 17.6 ml/min after 0.5 hour of operation. The conversion of butadiene was 55 percent and the yield of furan was 80 percent.

EXAMPLE 8

A gaseous stream of 46 percent by volume of butadiene in nitrogen was fed at a rate of 65 ml/min into 250 ml of an aqueous solution contained in a stirred reaction flask. The aqueous solution was initially at a pH less than 2 and 2.4 molar in cupric chloride and 0.05 molar in potassium iodide. Two ml of tetramethylethylenediamine were added to the aqueous solution. At a reaction temperature of 90°–95° C., furan was produced at a rate of 3.9–5.2 ml/min to give a furan concentration in the gaseous product stream of 6–8 percent by volume as analyzed by GC.

EXAMPLE 9

A gaseous stream of 50 percent by volume butadiene in nitrogen was fed at a rate of 150 ml/min into the reactor of Example 3 containing 400 ml of an aqueous solution which was 1 molar in cupric chloride, 0.5 molar in cuprous chloride, 1 molar in calcium chloride and 0.06 molar in potassium iodide. The acid content of the aqueous solution at the start of the reaction, as measured by titration with standard base, was 0.1 molar. During the course of the reaction, the acidity of the solution was followed by base titration of aliquot samples and the cupric ion concentration was calculated on the basis of the loss of one $Cu^{++}$ ion for each $H^+$ formed. The temperature of the aqueous solution was maintained at 75° C. Furan production was followed by GC with the rate of production shown in Table II.

TABLE II

| Reaction Time Min | Soln. Conc. - mole/l | | Furan Prod. | |
|---|---|---|---|---|
| | $H^+$ | $Cu^{++}$ | Vol. % | ml/min |
| 25 | .120 | .98 | 0.40 | 0.6 |
| 70 | .218 | .88 | 0.78 | 1.2 |
| 100 | .305 | .80 | 1.2 | 1.8 |

TABLE II-continued

| Reaction Time Min | Soln. Conc. - mole/l | | Furan Prod. | |
|---|---|---|---|---|
| | H+ | Cu++ | Vol. % | ml/min |
| 135 | .350 | .75 | 1.4 | 2.1 |
| 200 | .470 | .63 | 1.9 | 2.9 |
| 230 | .530 | .57 | 1.9 | 2.9 |

The reaction was stopped and air was fed into the aqueous solution for 30 min at a rate of 150 ml/min to oxidize the excess cuprous chloride in the solution (formed by the reduction of the cupric chloride during the reaction). After the cupric chloride concentration had been restored to its initial concentration, the flow of the butadiene-nitrogen gaseous mixture was resumed at the rate of 150 ml/min, but the aqueous solution was then maintained at a temperature of 85° C. Furan production was followed as before with the rate of production as a function of solution acidity and cupric ion content shown in Table III.

TABLE III

| Reaction Time Min | Soln. Conc. - mole/l | | Furan Prod. | |
|---|---|---|---|---|
| | H+ | Cu++ | Vol. % | ml/min |
| 24 | .175 | .925 | 1.1 | 1.7 |
| 65 | .355 | .75 | 2.5 | 3.8 |
| 110 | .50 | .60 | 5.1 | 7.7 |
| 130 | .59 | .51 | 5.1 | 7.7 |
| 145 | .63 | .47 | 4.4 | 6.6 |

The reaction was again stopped to oxidize excess cuprous chloride to its initial cupric chloride content by feeding air into the solution at a rate of 150 ml/min. After the cupric chloride concentration had been restored, the flow of the butadiene-nitrogen mixture was resumed at 150 ml/min, but the solution temperature was maintained at 95° C. Furan production was followed as before with the rate of production as a function of solution acidity and cupric ion content shown in Table IV.

TABLE IV

| Reaction Time Min | Soln. Conc. - mole/l | | Furan Prod. | |
|---|---|---|---|---|
| | H+ | Cu++ | Vol. % | ml/min |
| 20 | .245 | .855 | .9 | 1.4 |
| 35 | .335 | .765 | 2.7 | 4.1 |
| 50 | .44 | .66 | 6.5 | 9.8 |
| 65 | .53 | .57 | 9.8 | 14.7 |
| 80 | .67 | .43 | 9.0 | 13.5 |
| 95 | .73 | .37 | 6.5 | 9.8 |

EXAMPLE 10

The reactor of Example 3 was charged with 400 ml of an aqueous solution which was 1 molar in cupric chloride, 0.5 molar in cuprous chloride, 1 molar in calcium chloride and 0.06 molar in potassium iodide. Mixtures of butadiene (BD) in air, as shown in Table V below, were fed into the solution in the reactor at a rate of 150 ml/min. The progress of the reaction is shown in Table V.

TABLE V

| Reaction Time Hrs. | Temp. °C. | Soln. Acidity Mole/l | BD in Feed Vol. % | Furan Prod. | |
|---|---|---|---|---|---|
| | | | | Vol. % | ml/min |
| 0.25 | 95 | .12 | 46.6 | 1.5 | 2.3 |

TABLE V-continued

| Reaction Time Hrs. | Temp. °C. | Soln. Acidity Mole/l | BD in Feed Vol. % | Furan Prod. | |
|---|---|---|---|---|---|
| | | | | Vol. % | ml/min |
| 1.0 | 96 | .26 | 40.0 | 8.0 | 12.0 |
| 1.6 | 98 | .28 | 40.0 | 8.8 | 13.2 |
| 2.5 | 96 | .21 | 40.0 | 7.0 | 10.5 |
| 3.5 | 98 | .31 | 40.0 | 8.2 | 12.3 |
| 5.5 | 98 | .39 | 40.0 | 8.1 | 12.2 |
| 6.0 | 98 | .37 | 40.0 | 8.9 | 13.4 |
| 6.5 | 99 | .37 | 40.0 | 9.0 | 13.5 |
| 9.0 | 99.5 | .35 | 53.0 | 10.2 | 15.3 |
| *10.0 | 98.5 | .25 | 40.0 | 5.4 | 8.1 |
| 11.0 | 97 | .21 | 40.0 | 5.3 | 8.0 |
| 11.5 | 97 | .15 | 53.3 | 4.0 | 6.0 |
| 12.5 | 98 | .20 | 53.3 | 7.1 | 10.7 |
| 13.5 | 98 | .29 | 53.3 | 9.1 | 13.7 |

*Run stopped for the day and restarted the next morning.

This example shows a one-step reaction for the preparation of furan simultaneously with the oxidation of cuprous chloride to cupric chloride.

EXAMPLE 11

A gaseous mixture of 50 percent by volume butadiene in nitrogen was fed at a rate of 100 ml/min into the reactor of Example 1 containing 100 ml of an aqueous solution which was 1 molar in cupric bromide, 0.5 molar in cuprous bromide, 1 molar in sodium bromide and 0.12 molar in potassium iodide. The pH of the solution was 0.0 and the temperature during reaction was maintained at 95° C. After 45 minutes of operation, the furan concentration in the off-gases as measured by GC was 3.3 percent by volume produced at a rate of 3.3 ml/min.

EXAMPLE 12

This example illustrates the use of elemental iodine as an oxidizing agent to make cuprous chloride active.

A gaseous stream of 50 percent by volume butadiene in nitrogen was fed at a rate of 80 ml/min into the reactor of Example 1 containing 100 ml of an aqueous solution, having an initial pH of −0.2, which was 1 molar in cuprous chloride, 2 molar in sodium chloride, 0.3 molar in potassium iodide and 0.5 molar in elemental iodine. During the reaction, the temperature of the solution was maintained at 100° C. After one hour of operation, the gaseous product stream contained 4.5 percent by volume furan as measured by GC, produced at a rate of 3.6 ml/min. The conversion of butadiene was 10 percent and the yield of furan was 90 percent.

EXAMPLE 13

This example demonstrates the effect of iodide on the rates of reaction.

A mixture of 80 percent butadiene in a mixture of butadiene and air was fed at the rate of 100 ml/min to the reactor of Example 1 which contained a solution 2 molar in cupric chloride, 1 molar in cuprous chloride and 2 molar in calcium chloride. The pH of the reaction mixture was 0.0 and the temperature was 95° C. After 45 minutes of operation, furan was produced at the rate of 0.8 ml/min. When 0.06 mole of potassium iodide was added to the reaction mixture, the rate of furan production increased until it reached 5.1 ml/min after another hour of operation. This is a 6.3-fold increase in the rate of furan production.

EXAMPLE 14

A stream of 36.5 ml/min of 17 percent 1,3-t-pentadiene in nitrogen was obtained by sparging nitrogen at the rate of 30 ml/min through liquid trans-1,3-pentadiene at 0° C. This gas stream was fed to the reactor of Example 8 which contained 125 ml of a solution which was 2.4 molar in cupric chloride, 1.4 molar in sodium chloride and 0.05 molar in potassium iodide. The temperature in the reactor was 98° C. The gaseous product stream contained 0.5 percent of 2-methylfuran. The product stream was analyzed by gas chromatography and the identity of the product was established by comparison of the retention time with that of an authentic sample.

EXAMPLE 15

A gaseous feed of 80 ml/min of 19.5 percent isoprene(2-methyl-1,3-butadiene) in 11 percent oxygen and 69 percent nitrogen was provided by vaporizing liquid isoprene at the rate of 0.075 ml/min into a stream of 9.2 ml/min of oxygen and 54.0 ml/min of nitrogen. The gaseous feed was introduced through a gas dispersion tube to about 500 ml of an aqueous solution which was 1 molar in cupric chloride, 0.5 molar in cuprous chloride, 2 molar in calcium chloride, 0.4 molar in hydrogen chloride and 0.025 molar in potassium iodide which was stirred in a 1-liter flask at 103° C. The chromatograph of the product stream showed that its components were 0.5 percent carbon dioxide, 12.5 percent isoprene, 7.8 percent oxygen, 70.6 percent nitrogen and two new peaks. The reaction products were condensed in a trap cooled by dry ice-acetone. Analysis of the condensates by gas chromatography-mass spectroscopy identified one of the new peaks as 3-methylfuran.

EXAMPLE 16

A stream 100 ml/min of 50 percent butadiene in air was fed to a solution of 300 g acetonitrile, 200 g water, 0.5 mole cupric chloride, 0.5 mole cuprous chloride, 1.0 mole calcium chloride, 0.2 mole hydrogen chloride and 0.0125 mole potassium iodide. The gaseous feed was introduced through a gas dispersion tube into the stirred solution in a 1-liter flask which was heated at 80° C. After 2 hours of flow, analysis of the product stream by gas chromatography showed that it contained 0.32 percent furan.

EXAMPLE 17

A feed of 0.07 ml/min of liquid crotyl chloride and a gaseous feed of 150 ml/min of air and nitrogen were fed simultaneously to the reactor of Example 3 which contained 400 ml of an aqueous solution 1 molar in cupric chloride, 0.5 molar in cuprous chloride, 2 molar in calcium chloride, 0.06 molar in potassium iodide and 0.50 molar in hydrogen chloride. The reaction temperature was 95° C. The product stream from the reactor contained 3 percent furan and 9 percent butadiene.

EXAMPLE 18

1,4-Dichloro-2-butene (6.5 g, 0.05 mole) was introduced at the rate of 0.05 ml/min to the reactor of Example 1 which contained 100 ml of an aqueous solution 1 molar in cupric chloride, 1 molar in cuprous chloride, 2 molar in calcium chloride, 1 molar in cuprous chloride, 2 molar in calcium chloride and 0.13 molar in potassium iodide. The pH of the mixture was 0.5 and the temperature was 95° C. A stream of 100 ml/min of nitrogen was passed through the reactor. The gaseous product stream was passed through a trap cooled by a dry ice-acetone bath. The liquid which was collected in the trap contained 7 percent butadiene and 75 percent furan.

We claim:

1. In a process for preparing a furan compound, the improvement comprising contacting in a reaction zone (A) a diolefin of the formula:

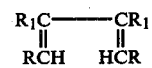

where
  each R is H or an alkyl group of 1–4 carbon atoms, and
  each $R_1$ is H, a halide or an alkyl group of 1–4 carbon atoms,
  with the proviso that the total number of carbon atoms does not exceed 8, or (B) a mono- or dihalo-substituted alkene of 4–8 carbon atoms, with an aqueous medium having a pH less than about 2 containing (1) iodine from elemental iodine or an iodine-containing compound, (2) copper having an average oxidation state between 1 and 2 and (3) a solubilizing agent for cuprous ion which is soluble in water and forms a water-soluble complex with cuprous ion.

2. The process of claim 1 wherein the diolefin is butadiene, chloroprene, 1,3-pentadiene or isoprene and the alkene is crotyl chloride.

3. The process of claim 1 wherein a diolefin is employed and it is butadiene.

4. The process of claim 1 wherein an alkene is employed and it is crotyl chloride.

5. The process of claim 1 wherein the iodine-containing compound is an alkali metal iodide.

6. The process of claim 1 or claim 2 or claim 5 wherein the reaction zone is at a temperature in the range of about 50°–125° C. and a pressure in the range of about 0.1–10 atmospheres.

7. The process of claim 2 wherein the solubilizing agent is at least one of an alkali metal chloride, alkaline earth metal chloride and ammonium chloride.

8. The process of claim 7 wherein the solubilizing agent concentration in the aqueous medium is in the range of about 0.01–5 gram moles per liter.

9. The process of claim 8 wherein the solubilizing agent is sodium chloride, calcium chloride or ammonium chloride.

10. The process of claim 2 wherein the iodine is from elemental iodine or an alkali metal iodide.

11. The process of claim 10 wherein the iodine concentration is in the range of about $1 \times 10^{-12}$–0.5 gram mole per liter.

12. The process of claim 11 wherein the iodine is from elemental iodine, potassium iodide or sodium iodide.

13. The process of claim 2 wherein the copper concentration in the aqueous medium is in the range of about 0.1–10 gram moles per liter.

14. The process of claim 1 or claim 2 or claim 8 or claim 11 or claim 13 wherein an oxygen-containing gas and the diolefin or halo-substituted alkene are contacted with the aqueous medium, the temperature of the reaction zone being in the range of about 50°–125° C. and at a pressure in the range of about 0.1–10 atmospheres.

15. A process for preparing a furan compound comprising passing butadiene, chloroprene, 1,3-pentadiene, isoprene or crotyl chloride through an aqueous solution having a pH less than about 0.5 at a temperature in the range of about 75°–105° C. and a pressure in the range of about 1–3 atmospheres, said solution having dissolved therein (1) at least one of an alkali metal iodide and elemental iodine at an iodine concentration in the range of 0.001–0.2 gram mole per liter; (2) chlorides of copper to provide copper at a concentration in the range of 0.5–3 gram moles per liter; and (3) an alkali metal chloride or an alkaline earth metal chloride at a concentration in the range of about 0.5–3 gram moles per liter.

16. The process of claim 15 wherein butadiene or crotyl chloride is passed through the solution.

17. The process of claim 16 wherein the iodine is from at least one of elemental iodine, sodium iodide and potassium iodide and the alkali metal chloride is sodium chloride and the alkaline earth metal chloride is calcium chloride.

18. The process of claim 15 or claim 16 or claim 17 wherein air is passed through the solution in an amount sufficient to provide about 1–2 moles of oxygen per mole of furan compound prepared.

19. In a process for preparing a furan compound by the catalytic oxidation of a diolefin, the improvement comprising (1) continuously contacting in a first reaction zone (A) a diolefin of the formula:

where
  each R is H or an alkyl group of 1–4 carbon atoms, and
  each $R_1$ is H, a halide or an alkyl group of 1–4 carbon atoms,
  with the proviso that the total number of carbon atoms does not exceed 8,
or (B) a mono- or diahlo-substituted alkene of 4–8 carbon atoms, with an aqueous medium having a pH less than about 2 containing (a) iodine from elemental iodine or an iodine-containing compound, (b) copper having an average oxidation state between 1 and 2 and (c) a solubilizing agent for cuprous ion which is soluble in water and forms a water-soluble complex with cuprous ion; (2) continuously removing reaction gases from the first reaction zone, removing furan compound product therefrom and returning unreacted diolefin or alkene to the first reaction zone; (3) continuously removing aqueous medium from the first reaction zone and passing it to a second reaction zone; (4) continuously contacting an oxygen-containing gas with the aqueous medium in the second reaction zone to oxidize cuprous ion in the aqueous medium to cupric ion; and (5) continuously returning oxygen-treated aqueous medium to the first reaction zone.

20. The process of claim 19 wherein the diolefin is butadiene, 1,3-pentadiene or isoprene and the alkene is crotyl chloride.

21. The process of claim 19 or claim 20 wherein the first reaction zone is at a temperature in the range of about 50°–125° C. and a pressure in the range of about 0.1–10 atmospheres.

22. The process of claim 19 wherein the aqueous medium is an aqueous solution having dissolved therein (1) iodine from at least one of an alkali metal iodide and elemental iodine at a concentration in the range of about $1 \times 10^{-12}$–0.5 gram mole per liter; (2) copper at a concentration in the range of about 0.1–10 gram moles per liter; and (3) an alkali metal chloride, alkaline earth metal chloride or ammonium chloride at a concentration in the range of about 0.01–5 gram mole per liter.

23. The process of claim 19 or claim 20 wherein the oxygen-containing gas is air.

24. The process of claim 19 wherein the diolefin is butadiene.

25. The process of claim 19 wherein the first reaction zone is at a temperature in the range of about 75°–105° C. and a pressure in the range of about 1–3 atmospheres.

26. The process of claim 24 or claim 25 wherein the aqueous medium is an aqueous solution having dissolved therein (1) at least one of an alkali metal iodide and elemental iodine at an iodine concentration in the range of 0.001–0.2 gram mole per liter; (2) chlorides of copper to provide copper at a concentration in the range of 0.5–3 gram moles per liter; and (3) an alkali metal chloride or an alkaline earth metal chloride at a concentration in the range of about 0.5–3 gram moles per liter.

* * * * *